United States Patent
Herman

(10) Patent No.: US 7,691,880 B2
(45) Date of Patent: Apr. 6, 2010

(54) METHYLPHENIDATE SOLUTION AND ASSOCIATED METHODS OF ADMINISTRATION AND PRODUCTION

(75) Inventor: Clifford J. Herman, St. Louis, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 10/554,133

(22) PCT Filed: Oct. 7, 2004

(86) PCT No.: PCT/US2004/033268

§ 371 (c)(1),
(2), (4) Date: Oct. 20, 2005

(87) PCT Pub. No.: WO2005/035000

PCT Pub. Date: Apr. 21, 2005

(65) Prior Publication Data

US 2006/0205776 A1    Sep. 14, 2006

(51) Int. Cl.
*A61K 31/445* (2006.01)

(52) U.S. Cl. .................................. 514/315; 514/319

(58) Field of Classification Search ............... 514/319, 514/315

See application file for complete search history.

(56) References Cited

U.S. PATENT DOCUMENTS

| | | | |
|---|---|---|---|
| 6,127,385 A * | 10/2000 | Midha et al. | 514/317 |
| 2002/0022640 A1 | 2/2002 | Zeldis et al. | |
| 2002/0103162 A1 * | 8/2002 | Epstein et al. | 514/79 |
| 2002/0132793 A1 | 12/2002 | Epsten et al. | |

FOREIGN PATENT DOCUMENTS

| EP | 1 163 907 A | 12/2001 |
|---|---|---|
| EP | 1 083 879 | 9/2004 |

* cited by examiner

*Primary Examiner*—Sreeni Padmanabhan
*Assistant Examiner*—Renee Claytor

(57) ABSTRACT

A methylphenidate solution and associated methods of administration and production, which includes methylphenidate and at least one organic acid dissolved in a solvent system, where the solvent system includes at least one non-aqueous solvent. The solvent system may include water. The non-aqueous solvent can include, but is not limited to polyols and glycols and associated mixtures thereof. Pharmaceutical additives such as flavorings, colorants, buffers, preservatives and mixtures thereof may be optionally added to the methylphenidate solution.

15 Claims, No Drawings

METHYLPHENIDATE SOLUTION AND ASSOCIATED METHODS OF ADMINISTRATION AND PRODUCTION

FIELD OF THE INVENTION

The present invention relates to a methylphenidate solution, and more particularly to a pharmaceutically acceptable methylphenidate solution that exhibits sufficient chemical stability to provide a satisfactory shelf life.

BACKGROUND OF THE INVENTION

Methylphenidate HCl, CAS No. 298-59-9, is prescribed primarily to treat attention-deficit/hyperactivity disorder in children. Methylphenidate HCl is currently available as a solid based capsule or tablet, typically in 5 mg or higher dosages. Solid based formulations have inherent limitations, as capsules and tablets can be difficult to subdivide. It is therefore difficult to precisely administer any dosage other than multiples of the standard available dosages. Further, capsules and tablets present swallowing difficulties for some patients. A liquid formulation of methylphenidate HCl is therefore desirable.

Unfortunately, methylphenidate HCl has not been chemically stable in conventional liquid vehicles. The primary route of methylphenidate HCl degradation in solution is hydrolysis resulting in the formation of threo-α-phenyl-2-piperidineacetic acid (major) and 2-piperidineacetic acid, α-phenyl-methyl ester (minor) compounds. In addition to stability, the methylphenidate HCl solution must be pharmaceutically acceptable and have an acceptable taste.

It is therefore desirable to provide a methylphenidate HCl solution that is chemically stable, pharmaceutically acceptable and palatable.

SUMMARY OF THE INVENTION

In a first aspect of the present invention, a methylphenidate solution is disclosed. This solution comprises, in the preferred embodiment, a therapeutic amount of methylphenidate HCl. The methylphenidate concentration is typically determined by the desired dosage volume. The preferred solution further comprises from about 0.5 mg/ml to about 5.0 mg/ml of at least one organic acid that enhances taste by providing tartness. The methylphenidate and the organic acid are dissolved in a solvent system that comprises at least one non-aqueous solvent. This methylphenidate solution is chemically stable.

In another aspect of this invention, a method for administering methylphenidate as an oral solution is disclosed. This method includes, in a preferred embodiment, preparing a solution containing a therapeutic amount of methylphenidate HCl and administering the methylphenidate HCl solution.

These are merely two illustrative aspects of the present invention and should not be deemed an all-inclusive listing of the innumerable aspects associated with the present invention. These and other aspects will become apparent to those skilled in the art in light of the following disclosure.

DETAILED DESCRIPTION OF THE INVENTION

Methylphenidate HCl is the preferred main component that is utilized with the present invention. While the hydrochloride form of methylphenidate is most commonly utilized currently, it is understood that the present invention would be applicable to any therapeutic form of methylphenidate compound, including but not limited to methylphenidate base and pharmaceutically acceptable salts of methylphenidate.

The concentration of methylphenidate HCl is variable and may be determined by the desired dosage and volume. For example, a 1 mg/mL methylphenidate HCl solution will yield a 5 mg dose per teaspoon oral dose, and a 2 mg/ml methylphenidate HCl solution will yield a 10 mg dose per teaspoon oral dose. These concentrations correspond to two dosages currently available, but can go higher. However, since the methylphenidate HCl is delivered in a solution, the dosage can be easily manipulated to prescribe a non-standard dosage. The concentration of methylphenidate HCl in the solution is preferably about 0.1 mg/ml to about 10.0 mg/ml.

A completely aqueous solvent system is not suitable for a methylphenidate HCl solution due to problems with solubility and stability. It is therefore necessary to provide a pharmaceutically acceptable solvent system in which the methylphenidate HCl is sufficiently stable to provide a suitable shelf life. In a preferred embodiment, the solvent system is at least about 50% non-aqueous solvent. The percentages given herein relate to the solvent system are weight/weight percentages of the solvent system only unless otherwise specified.

Another consideration in the formulation of the solvent system is taste. The overall taste feature of the solution is especially important in the area of pediatric medicine.

Glycol compounds have been found to greatly enhance the stability of methylphenidate HCl solutions. The glycol may be propylene glycol, polyethylene glycol or any other pharmaceutically acceptable polyalkylene glycol product such as those known in the art as the "PEG" series, or mixtures thereof. The PEG compounds are defined as chemical structures having 2 or 3 carbon atoms in the alkylene moiety of their chemical structures and a mean molecular weight of 200 to 4000.

A 100% glycol solution would provide a chemically stable methylphenidate HCl solution, however, the resulting solution would present other problems. At this level certain glycols would no longer be pharmaceutically acceptable. Propylene glycol, for example, would exceed acceptable safety levels. Furthermore, the taste would be less than desirable. While propylene glycol improves methylphenidate HCl stability, it imparts a bad taste at higher concentrations. Polyethylene glycol (hereinafter PEG) is therefore preferred for taste and safety purposes. In a preferred embodiment of the present invention the solvent system utilizes from about 10% to about 70% glycol, with about 10% to about 30% being more preferred, about 10% to about 20% being most preferred and about 15% being the optimal value.

Polyol compounds provide another pharmaceutically acceptable non-aqueous solvent. Acceptable polyol products include but are not limited to those having more than two hydroxyl groups in their chemical structures such as glycerin, sorbitol or simple sugars such as glucose and fructose and mixtures thereof. These polyols have an added feature in that they impart a sweet taste to the overall solution and act as a preservative. In a preferred embodiment, the polyol is glycerin. The solvent system of this invention includes, from about 30% to about 70% being preferred, about 40% to about 60% being more preferred, about 45% to about 55% being most preferred and about 50% being the optimal value.

While the solvent system may be completely non-aqueous, the addition of water improves the taste of the solution. In a preferred embodiment, the solvent system includes as much as about 50% water, with about 10% to about 45% being more preferred, about 30% to about 40% being most preferred and about 35% being the optimal value.

The organic acid included in the chemically stable methylphenidate HCl solution of the present invention preferably is any suitable pharmaceutically acceptable organic acid. Suitable organic acids include but are not limited to acetic acid, ascorbic acid, citric acid, fumaric acid, malic acid, succinic acid, tartaric acid and mixtures thereof. Organic acids, which enhance the taste of the solution, are especially useful. Citric acid, for example, adds tartness that is a taste enhancer, and may play a role in overall stability of the solution. The concentration of the organic acid in the solvent system is preferably in the range of about 0.5 mg/ml to about 5.0 mg/ml, with about 0.5 mg/ml to about 3.0 mg/ml being more preferred, about 0.5 mg/ml to about 1.5 mg/ml being most preferred and about 1.0 mg/ml being the optimal value.

Additional pharmaceutically acceptable additives may be added to the methylphenidate HCl solution, as is known in the art. These additives include but are not limited to flavorings, colorants, buffers and preservatives. The methylphenidate solution of the present invention may be stored in any non-reactive container. Glass and/or plastic containers are presently preferred.

The primary degradation product of the methylphenidate HCl solution is threoacetic acid, with a minor 2-piperidineacetic acid, α-phenyl-methyl ester component. Other minor reaction products have been noted, but are statistically insignificant.

The resulting methylphenidate HCl solution would typically be administered orally. However, the methylphenidate HCl solution could be administered intravenously or by inhalation if properly nebulized. Further, the methylphenidate HCl solution of the present invention may be adapted for use in a gel cap.

A therapeutically effective amount of methlphenidate HCl in a liquid solution may be administered to a patient having a disorder treatable by methylphenidate. Such disorders include, but are not limited to, behavioral disorders, Attention Deficit Disorder, Attention Deficit Hyperactivity Disorder, depression, specific dyslexias, brain dysfunction, cognitive decline in AIDS and AIDS related conditions, alertness in geriatric and Alzheimers patients. Further, a therapeutically effective amount of methlphenidate HCl in a liquid solution may be administered for use in recovery in stroke victims. The methylphenidate HCl solution may be stored in a non-reactive container for a predetermined period of time prior to administering the methylphenidate solution.

As is seen in the following examples, the methylphenidate HCl solution of the present invention is stable at 25° C. and also under accelerated storage conditions. Although the presently preferred solutions undergo some hydrolysis, the extrapolated hydrolysis rate predicts at least a two-year shelf life at 25° C.

EXAMPLE 1

A 1.0 mg/ml methylphenidate HCl was prepared. Glycerin, USP, 630.09 g and 350.03 g deionized water were placed into a beaker and stirred until a homogeneous solution was formed. Polyethylene glycol 1450, 181.45 g was added and stirred until dissolved. Citric acid, USP, 2.50 g was added and stirred until dissolved. Methylphenidate HCl, USP, 1.01 g added and stirred to dissolve. A grape flavoring was added and stirred to incorporate. The resulting formulation was transferred to HDPE containers in 30 ml quantities and the containers were sealed using an induction sealer. Samples were stored at 25° C./60% RH (T1) and 40° C./75% RH (T2). Samples were analyzed by HPLC for threoacetic acid (TA), 2-piperidineacetic acid, α-phenyl-methyl ester (E1), and methylphenidate at 2, 3, 6 and 9 month intervals. The samples were also tested for pH, color and odor. The data from Example 1 is outlined in the following Table 1:

TABLE 1

| Methylphenidate HCl 1.0 mg/ml | | | APHA Standard | | | | Methylphenidate |
|---|---|---|---|---|---|---|---|
| Months | Temp | pH | Color | Odor | µg/ml TA | µg/ml E1 | % recovered |
| 0 |  | 3.28 | 5 | 1 | 0.5 | — | 100.76 |
| 2 | T1 | 3.18 | 5 | 1 | 1.91 | 2.11 | 100.50 |
| 2 | T2 | 3.18 | 5 | 1 | 8.91 | 0.64 | 97.49 |
| 3 | T1 | 3.10 | 5 | 2 | 2.6 | 0.3 | 99.93 |
| 3 | T2 | 3.02 | 5 | 2 | 11.7 | 1.6 | 97.22 |
| 6 | T1 | 3.01 | 5 | 2 | 4.9 | 0.1 | 99.92 |
| 6 | T2 | 2.98 | 5–10 | 1 | 22.6 | 3.2 | 93.94 |
| 9 | T1 | 2.97 | 5–10 | 2 | 6.8 | 0.2 | 97.71 |
| 9 | T2 | 2.80 | 5–10 | 2 | 31.6 | 1.6 | 89.31 |

T1 = 25° C./
T2 = 40° C./
1 = grape
2 = faint grape
3 = sour grape

EXAMPLE 2

A 2.0 mg/ml methylphenidate HCl was prepared. Glycerin, USP, 630.03 g and 349.99 g deionized water were placed into a beaker and stirred until a homogeneous solution was formed. Polyethylene glycol 1450, 181.50 g was added and stirred until dissolved. The citric acid, USP, 2.50 g was added and stirred until dissolved. Methylphenidate HCl, USP, 2.02 g added and stirred to dissolve. A grape flavoring was added and stirred to incorporate. The solutions were treated and analyzed as in Example 1.

The data from Example 2 is outlined in the following Table 2:

TABLE 2

| Methylphenidate HCl 1.0 mg/ml | | | APHA Standard | | | | Methylphenidate |
|---|---|---|---|---|---|---|---|
| Months | Temp | pH | Color | Odor | µg/ml TA | µg/ml E1 | % recovered |
| 0 |  | 3.21 | 5 | 1 | 0.6 | — | 100.28 |
| 2 | T1 | 3.12 | 5 | 1 | 3.77 | 2.22 | 99.85 |
| 2 | T2 | 3.12 | 5 | 1 | 18.70 | 1.11 | 97.61 |
| 3 | T1 | 3.04 | 5 | 2 | 5.5 | 0.4 | 99.92 |
| 3 | T2 | 3.00 | 5 | 2 | 24.4 | 3.0 | 97.45 |
| 6 | T1 | 2.98 | 5 | 2 | 10.2 | 0.6 | 100.49 |
| 6 | T2 | 3.00 | 5–10 | 2 | 47.7 | 6.0 | 94.81 |
| 9 | T1 | 2.87 | 5–10 | 3 | 14.0 | 0.3 | 99.37 |
| 9 | T2 | 2.76 | 5–10 | 3 | 67.6 | 3.0 | 91.63 |

T1 = 25° C./
T2 = 40° C./
1 = grape
2 = faint grape
3 = sour grape

EXAMPLE 3

Three 2.0 mg/ml methylphenidate HCl solutions were prepared as in Example 2, resulting in the following compositions:

| Component | Concentration (mg/ml) |
|---|---|
| Methylphenidate HCl, USP | 2.0 |
| Glycerin, USP | 630 |
| PEG 1450, NF | 181.5 |
| Deionized water | 350 |
| Citric acid, USP | 0.5, 2.5 and 5.0 |
| Grape flavoring | 0.5 |

The solutions were analyzed as in Examples 1 and 2 after storage at 25° C., 30° C., 40° C. and 50° C. at one and two month intervals. This data is outlined in the following Table 3:

TABLE 3

| Methylphenidate HCl 1.0 mg/ml | | Citric acid | | APHA Standard | | | µg/ml | µg/ml | Methylphenidate |
|---|---|---|---|---|---|---|---|---|---|
| Time | Temp | mg/ml | pH | Color | Odor | | TA | E1 | % recovered |
| 1 month | T1 | 0.5 | 3.29 | 5 | 1 | | 2.4 | 0.2 | 99.70 |
|  | T1 | 2.5 | 2.90 | 5 | 1 | | 2.8 | 0.0 | 97.24 |
|  | T1 | 5.0 | 2.71 | 5 | 1 | | 3.6 | 0.0 | 98.89 |
|  | T2 | 0.5 | 3.32 | 5 | 1 | | 3.0 | 0.4 | 99.75 |
|  | T2 | 2.5 | 2.89 | 5 | 1 | | 3.4 | 0.1 | 99.41 |
|  | T2 | 5.0 | 2.72 | 5 | 1 | | 4.2 | 0.0 | 99.58 |
|  | T3 | 0.5 | 3.35 | 5 | 1 | | 8.8 | 1.7 | 98.65 |
|  | T3 | 2.5 | 2.91 | 5 | 1 | | 8.7 | 0.8 | 98.36 |
|  | T3 | 5.0 | 2.75 | 5 | 1 | | 11.1 | 0.6 | 98.53 |
|  | T4 | 0.5 | 3.31 | 5 | 1 | | 23.7 | 6.2 | 98.31 |
|  | T4 | 2.5 | 2.93 | 5 | 1 | | 21.2 | 2.9 | 98.44 |
|  | T4 | 5.0 | 2.78 | 5 | 1 | | 26.6 | 2.4 | 97.35 |
| 2 months | T1 | 0.5 | 3.29 | 5 | 2 | | 5.0 | 0.6 | 98.29 |
|  | T1 | 2.5 | 2.86 | 5 | 1 | | 6.1 | 0.0 | 98.91 |
|  | T1 | 5.0 | 2.70 | 5 | 2 | | 8.1 | 0.0 | 98.83 |
|  | T2 | 0.5 | 3.27 | 5 | 1 | | 6.0 | 0.7 | 98.29 |
|  | T2 | 2.5 | 2.83 | 5 | 1 | | 7.1 | 0.3 | 100.29 |
|  | T2 | 5.0 | 2.67 | 5 | 1 | | 9.5 | 0.3 | 99.60 |
|  | T3 | 0.5 | 3.30 | 5 | 2 | | 24.4 | 5.1 | 96.74 |
|  | T3 | 2.5 | 2.87 | 5 | 2 | | 24.1 | 2.3 | 97.41 |
|  | T3 | 5.0 | 2.71 | 5 | 2 | | 30.4 | 1.9 | 97.57 |
|  | T4 | 0.5 | 3.02 | 5 | 3 | | 62.1 | 15.6 | 91.53 |
|  | T4 | 2.5 | 2.85 | 5 | 3 | | 59.1 | 9.3 | 91.72 |
|  | T4 | 5.0 | 2.70 | 5 | 3 | | 71.1 | 7.8 | 92.38 |

T1 = 25° C./60% RH
T2 = 30° C.
T3 = 40° C./75% RH
T4 = 50° C.
1 = grape
2 = faint grape
3 = sour grape Having described the invention in detail, those skilled in the art will appreciate that modifications may be made of the invention without departing from its spirit and scope. Therefore, it is not intended that the scope of the invention be limited to the specific embodiments described. Rather, it is intended that the appended claims and their equivalents determine the scope of the invention.

The invention claimed is:

1. An oral methylphenidate HCl solution comprising:
   about 0.1 mg/ml to about 10.0 mg/ml methylphenidate HCl; and
   about 0.5 mg/ml to about 5.0 mg/ml of at least one organic acid, the methylphenidate HCl and the at least one organic acid being dissolved in a solvent system, the solvent system comprising:
   about 10% to about 45% water;
   about 30% to about 70% of at least one polyol solvent;
   about 10% to about 70% of at least one glycol solvent; and
   wherein the oral methylphenidate HCl solution is storage stable.

2. The methylphenidate HCl solution according to claim 1, wherein the at least one organic acid is selected from the group consisting of acetic acid, ascorbic acid, citric acid, fumaric acid, malic acid, succinic acid, tartaric acid and mixtures thereof.

3. The methylphenidate HCL solution according to claim 1, wherein the at least one polyol solvent is selected from the group consisting of glycerin, sorbitol, sucrose, fructose and mixtures thereof.

4. The methylphenidate HCl solution according to claim 1, wherein the at least one glycol solvent is selected from the group consisting of propylene glycol, polyalkylene glycol products and mixtures thereof.

5. The methylphenidate HCl solution according to claim 1, further including at least one pharmaceutical additive selected from the group consisting of flavorings, colorants, buffers, preservatives and mixtures thereof.

6. An oral methylphenidate HCl solution comprising:
   about 0.1 mg/ml to about 10.0 mg/ml methylphenidate HCl; and about 0.5 mg/ml to about 3.0 mg/ml of at least one organic acid, the methylphenidate HCl and the at least one organic acid being dissolved in a solvent system, the solvent system comprising:

about 10% to about 45% water;

about 40% to about 60% of at least one polyol solvent;

about 10% to about 30% of at least one glycol solvent; and wherein the oral methylphenidate HCl solution is storage stable.

7. The methylphenidate HCl solution according to claim 6, wherein at least one organic acid is selected from the group consisting of acetic acid, ascorbic acid, citric acid, fumaric acid, malic acid, succinc acid, tartaric acid and mixtures thereof.

8. The methylphenidate HCl solution according to claim 6, wherein the at least one polyol solvent is selected from the group consisting of glycerin, sorbitol, sucrose, fructose and mixtures thereof.

9. The methylphenidate HCl solution according to claim 6, wherein the at least one glycol solvent is selected from the group consisting of propylene glycol, polyalkylene glycol products and mixtures thereof.

10. The methylphenidate HCl solution according to claim 6, further including at least one pharmaceutical additive selected from the group consisting of flavorings, colorants, buffers, preservatives and mixtures thereof.

11. An oral methylphenidate HCl solution comprising:

about 0.1 mg/ml to about 10.0 mg/ml methylphenidate HCl; and about 0.5 mg/ml to about 1.5 mg/ml of at least one organic acid, the methylphenidate HCl and the at least one organic acid being dissolved in a solvent system, the solvent system comprising:

about 30% to about 40% water;

about 45% to about 55% of at least one polyol solvent;

about 10% to about 20% of at least one glycol solvent; and wherein the oral methylphenidate HCl solution is storage stable.

12. The methylphenidate HCl solution according to claim 11, wherein the at least one organic acid includes citric acid.

13. The methylphenidate HCl solution according to claim 11, wherein the at least one polyol solvent includes glycerin.

14. The methylphenidate HCl solution according to claim 11, wherein the at least one glycol solvent includes polyethylene glycol.

15. The methylphenidate HCl solution according to claim 11, further including at least one pharmaceutical additive selected from the group consisting of flavorings, colorants, buffer, preservatives and mixtures thereof.

* * * * *